(12) United States Patent
Dultz (10) Patent No.: US 7,799,558 B1
(45) Date of Patent: *Sep. 21, 2010

(54) LIGAND BINDING ASSAYS ON MICROARRAYS IN CLOSED MULTIWELL PLATES

(76) Inventor: Shane C. Dultz, 4401 Yorkfield Ct., Westlake Village, CA (US) 91361

(*) Notice: Subject to any disclaimer, the term of this patent is extended or adjusted under 35 U.S.C. 154(b) by 459 days.

This patent is subject to a terminal disclaimer.

(21) Appl. No.: 11/752,056

(22) Filed: May 22, 2007

(51) Int. Cl.
*G01N 33/543* (2006.01)

(52) U.S. Cl. .................. 435/287.2; 422/57; 422/58; 435/287.9; 435/288.3; 435/288.4; 436/809

(58) Field of Classification Search .................. None
See application file for complete search history.

(56) References Cited

U.S. PATENT DOCUMENTS

| | | |
|---|---|---|
| 1,637,141 A | 7/1927 | Cooper |
| 3,858,616 A | 1/1975 | Thiery et al. |
| 4,146,365 A * | 3/1979 | Kay et al. ..................... 422/57 |
| 4,238,565 A | 12/1980 | Hornby et al. |
| 4,256,834 A | 3/1981 | Zuk et al. |
| 4,508,832 A | 4/1985 | Carter et al. |
| 5,164,589 A | 11/1992 | Sjoedin |
| 5,229,833 A | 7/1993 | Stewart |
| 5,234,769 A | 8/1993 | Shevlin |
| 5,255,075 A | 10/1993 | Cush |
| 5,313,264 A | 5/1994 | Ivarsson et al. |
| 5,341,215 A | 8/1994 | Seher |
| 5,437,840 A | 8/1995 | King et al. |
| 5,446,534 A | 8/1995 | Goldman |
| 5,483,346 A | 1/1996 | Butzer |
| 5,485,277 A | 1/1996 | Foster |

(Continued)

FOREIGN PATENT DOCUMENTS

AU 742417 2/2000

(Continued)

OTHER PUBLICATIONS

Tadashi Saitoh, et al."Optical Characterization of Very Thin Hydrogenated Amorphous Silicon Films Using Spectroscopic Ellipsometry"; Japanese Journal of Applied Physics; vol. 30, No. 11B, Nov. 1991. pp. L1914-L1916.

(Continued)

*Primary Examiner*—Christopher L Chin
(74) *Attorney, Agent, or Firm*—Haynes and Boone, LLP (57) ABSTRACT

Multiwell plates commonly used for immunoassay are increased in capacity and adapted for ease and speed of testing by forming a plurality of solid posts in each well of a plate. The posts and plate material and the dimensions of the posts are chosen to allow the immobilization of ligand patterns on an exterior wall of a post in a well and to permit a collimated beam of light directed to the post in a direction to achieve total internal reflection from a wall to generate an evanescent field in the plane of the ligands immobilized on the exterior wall of the post. The reflected light carries an image of localized intensity variations due to binding events between the ligand patterns and analytes in a sample introduced into a well. A cover plate seals the wells and provides for through holes for introducing sample material to the wells.

13 Claims, 9 Drawing Sheets

U.S. PATENT DOCUMENTS

| | | | |
|---|---|---|---|
| 5,491,097 | A | 2/1996 | Ribi et al. |
| 5,491,556 | A | 2/1996 | Stewart et al. |
| 5,573,956 | A | 11/1996 | Hanning |
| 5,593,130 | A | 1/1997 | Hansson et al. |
| 5,633,724 | A | 5/1997 | King et al. |
| 5,641,640 | A | 6/1997 | Hanning |
| RE35,716 | E | 1/1998 | Stapleton et al. |
| 5,753,518 | A | 5/1998 | Karlsson |
| 5,796,858 | A | 8/1998 | Zhou et al. |
| 5,813,439 | A | 9/1998 | Herrero et al. |
| 5,856,873 | A | 1/1999 | Naya et al. |
| 5,922,594 | A | 7/1999 | Loefas |
| 5,922,604 | A | 7/1999 | Stapleton et al. |
| 5,955,729 | A | 9/1999 | Nelson et al. |
| 5,965,456 | A | 10/1999 | Malmqvist et al. |
| 5,972,612 | A | 10/1999 | Malmqvist et al. |
| 6,008,010 | A | 12/1999 | Greenberger et al. |
| 6,008,893 | A | 12/1999 | Roos et al. |
| 6,026,053 | A | 2/2000 | Satorius |
| 6,045,996 | A | 4/2000 | Cronin et al. |
| 6,065,501 | A | 5/2000 | Feret et al. |
| 6,127,183 | A | 10/2000 | Ivarsson et al. |
| 6,140,044 | A | 10/2000 | Bessemer et al. |
| 6,143,513 | A | 11/2000 | Loefas |
| 6,143,574 | A | 11/2000 | Karlsson et al. |
| 6,197,595 | B1 | 3/2001 | Anderson et al. |
| 6,200,814 | B1 | 3/2001 | Malmqvist et al. |
| 6,207,381 | B1 | 3/2001 | Larsson et al. |
| 6,253,793 | B1 | 7/2001 | Dupoiron et al. |
| 6,277,330 | B1 | 8/2001 | Liu et al. |
| 6,289,286 | B1 | 9/2001 | Andersson et al. |
| 6,354,333 | B1 | 3/2002 | Dupoiron et al. |
| 6,355,429 | B1 | 3/2002 | Nygren et al. |
| 6,415,725 | B1 | 7/2002 | Yoshikazu |
| 6,475,809 | B1 | 11/2002 | Wagner et al. |
| 6,493,097 | B1 | 12/2002 | Ivarsson |
| 6,503,760 | B2 | 1/2003 | Malmqvist et al. |
| D472,644 | S | 4/2003 | Dawson et al. |
| 6,549,011 | B2 | 4/2003 | Flatt |
| 6,589,798 | B1 | 7/2003 | Loefas |
| 6,594,011 | B1 | 7/2003 | Kempen |
| D480,149 | S | 9/2003 | Dawson et al. |
| 6,698,454 | B2 | 3/2004 | Sjoelander et al. |
| 6,710,870 | B1 | 3/2004 | Marowsky et al. |
| 6,714,303 | B2 | 3/2004 | Ivarsson |
| 6,806,051 | B2 | 10/2004 | Ellson |
| 6,810,286 | B2 | 10/2004 | Donovan et al. |
| 6,833,920 | B2 | 12/2004 | Rassman et al. |
| 6,859,280 | B2 | 2/2005 | Kempen |
| 6,882,420 | B2 | 4/2005 | Rassman et al. |
| 6,981,526 | B2 | 1/2006 | Glejbol et al. |
| 7,045,287 | B2 | 5/2006 | Smith et al. |
| 7,193,711 | B2 | 3/2007 | Rassman et al. |
| 7,195,872 | B2 * | 3/2007 | Agrawal et al. ............... 435/6 |
| 2002/0019019 | A1 | 2/2002 | Hamalainen et al. |
| 2002/0154311 | A1 | 10/2002 | Ivarsson |
| 2002/0182717 | A1 | 12/2002 | Karlsson |
| 2003/0022388 | A1 | 1/2003 | Roos et al. |
| 2003/0067612 | A1 | 4/2003 | Ivarsson |
| 2003/0112432 | A1 | 6/2003 | Yguerabide et al. |
| 2003/0205681 | A1 | 11/2003 | Modlin |
| 2004/0002167 | A1 | 1/2004 | Andersson et al. |
| 2004/0012676 | A1 | 1/2004 | Weiner et al. |
| 2004/0023247 | A1 | 2/2004 | Xu et al. |
| 2004/0030504 | A1 | 2/2004 | Helt et al. |
| 2004/0038268 | A1 | 2/2004 | Pirrung et al. |
| 2005/0148063 | A1 | 7/2005 | Cracauer et al. |

FOREIGN PATENT DOCUMENTS

| | | |
|---|---|---|
| WO | WO 8911057 | 11/1989 |
| WO | WO 9100467 | 1/1991 |
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

"Handbook of Optics", Michael Bass Editor in Chief, by The Optical Society of America; vol. 1; pp. 4.23, 4.24; 1995 McGraw-Hill, Inc.

Bass, et al. "Handbook of Optics", by The Optical Society of America; vol. 1; Section 41.10; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press 1980.

Eggins, "Biosensors: An Introduction", pp. 112-113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3-4 pp. 439-449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7-D13, Papers No. 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50, 1992.

Ulf Jonsson et al. "Flow-Injection Ellipsometry—An in Situ Method for the Study of Biomolecular Adsorption and Interaction at Solid Surfaces," Colloids and Surfaces, 13 (1985) pp. 333-339, 1985 Elsevier Science Publishers BV, Amsterdam, The Netherlands.

Jonsson, Ulf et al. "Biosensors Based on Surface Concentration Measuring Devices-The Concept of Surface Concentration" Progress in Colloid and Polymer Sci. vol. 70, pp. 96-100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International, Inc., Sunnyvale, California, USA, A BioTechniques Books Publication, Eaton Publishing, pp. 10-11, 2000.

Harland G. Tompkins, et al. "Spectroscopic Ellipsometry and Reflectometry A User's Guide" A Wiley-Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381-1351, 1988 Academic Press, Inc. Harcourt Brace Jovanovich, Publishers.

CH Striebel et al. "Characterization of Biomembranes by Spectral Ellipsometry, Surface Plasmon Resonance and Interferometry with Regard to Biosensor Application", Biosensors & Bioelectronics 9, pp. 139-146, 1994 Elsevier Science Publishers Ltd.

T.A. Ruzgas et al. "Ellipsometric Immunosensors for the Determination of γ-Interferon and Human Serum Albumin", Biosensors & Bioelectronics 7, pp. 305-308, 1992 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd.

John F. Place et al. "Opto-electronic Immunosensors: A Review of Optical Immunoassay At Continuous Surfaces", Biosensors 1, pp. 321-353, 1985 Elsevier Applied Science Publishers Ltd., England.

A. Brecht et al. "Biosensors: Fundamentals, Technologies and Applications" GBF Monographs, vol. 17, pp. 174-178, 1991 Germany.

Hakan Nygren et al. "Kinetics of Antibody-Binding to Surface-Immobilized Antigen: Influence of Mass Transport on the Enzyme- Linked Immunosorbent Assay (ELISA)", Journal of Colloid and Interface Science, vol. 107, No. 2 pp. 560-566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70-78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81-91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163-181, 1995 Humana Press Inc.

G. Elender et al. "Wetting and Dewetting of Si/SiO2-Wafers by Free and Lipid-Monolayer Covered Aqueous Solutions Under Controlled Humidity", Journal de Physique, II France 4 pp. 455-479, Mar. 1994.

C.F. Mandenius et al. "Coupling of Biomolecules to Silicon Surfaces for use in ellipsometry and other related techniques", Methods in Enzymology, vol. 137, pp. 389-394, 1988 Academic Press, Inc.

A.W. Flounders et al. "Patterning of immobilized antibody layers via photolithography and oxygen plasma exposure", Biosensors and Bioelectronics, vol. 12, No. 6 pp. 447-456, 1997 Elsevier Science Ltd., Great Britain.

A. Ahluwalia et al. "A comparative study of protein immobilization techniques for optical immunosensors", Biosensors and Bioelectronics 7, (1991) pp. 207-214, 1992 Elsevier Science Publishers Ltd.

Dr. Rudolf Oldenbourg "Metamorph Imaging System", http://www.image1.com/products/ metapolscope/ Universal Imaging Corporation Last Updated Jun. 10, 1999 pp. 1-2.

Dr. Rudolf Oldenbourg "A new view on polarization microscopy", Nature, vol. 381, pp. 811-812, Jun. 27, 1996.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvall et al. "Complement activation by 3-mercapto-1,2-propanediol immobilized on gold surfaces", Biomaterials vol. 17, No. 10 pp. 1001-1007, 1995 Elsevier Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Gratings, Ruled and Holographic", Applied Optics and Optical Engineering, vol. IX, pp. 33-71, Bausch and Lomb, Inc., Rochester, New York 1983 Academic Press, Inc.

Willems, Goerge M., et al., Adsorption and Conversion of Prothrombin on a Rotating Disc, Blood, Jul. 15, 1993, vol. 82, No. 2, pp. 497-504.

* cited by examiner

LIGAND BINDING ASSAYS ON MICROARRAYS IN CLOSED MULTIWELL PLATES

CROSS-REFERENCE TO RELATED APPLICATIONS

This application is related to U.S. application Ser. No. 11/696,369, filed Apr. 4, 2007, the full disclosure of which (including all references incorporated by reference therein) is incorporated by reference herein for all purposes.

FIELD OF THE INVENTION

This invention relates to characterizing molecular binding events for performing ligand binding assays and more particularly to systems employing ligand spots or microarrays in a closed multiwell format.

BACKGROUND

U.S. Pat. No. 6,594,011 issued Jul. 15, 2003, the entirety of which is incorporated by reference herein for all purposes, discloses an imaging apparatus and method for real time imaging ellipsometry for high throughput sensing of binding events useful in molecular interaction analysis including biotech applications. The apparatus disclosed employs the immobilization of an array of binding or capture molecules ("ligands") on a planar surface of a transparent substrate and the use of a beam of polarized light directed at the underside of the surface in a manner to achieve total internal reflection (TIR) and generate an evanescent field in the plane of the ligands. The ligands are exposed to a biological sample and analytes in the biological sample bind to different patterns of the immobilized ligands in a manner to change the polarization at locations in the array at which binding occurs. An image of the array is compared with a stored image of the initial light polarization shifts to determine the location and magnitude of binding events within the array, thus identifying and quantitating the analytes present in the biological sample.

The apparatus for implementing the foregoing technique typically employs a prism or gratings to achieve the requisite TIR generated evanescent field, the prism being the most practical implementation.

TIR imaging ellipsometry works well for fields of view up to 1-2 $cm^2$, which permits real time imaging of tens of thousands of binding events simultaneously. However, there is a need to be able to image or scan areas which are much larger, such as 128 mm×86 mm (e.g. the area of a 384 well or a 96 well multiwell plate), to permit lower costs per test and for multiple tests per patient for large numbers of patients simultaneously, which is increasingly a requirement for clinical diagnostics and personalized medicine. Obviating the need for a prism simplifies both the instrument and disposable multiwell plate.

Also, it is well known in the art to label a hybridized target or probe by, for example, adding a molecule, either being conjugated to, bound to, or associated with the target. Labels include reporter molecules that can be detected directly by virtue of generating a signal. Examples include but are not limited to fluorophores, dyes, chemiluminescent probes, radioactive atoms or molecules, magnetic particles and quantum dots. The detection of labeled target molecules in a binding assay may employ total internal reflection as a way of exciting fluorophores, for example, which could then be detected from above or below the assay surface. There are examples in the literature which demonstrate the benefits of detecting fluorophore emission at angles close to the critical angle (see e.g., http://www.olympusmicro.com/primer/techniques/fluorescence/tirf/tirfintro.html) in such a total internal reflection configuration. The reason for this has to do with the anisotropic fluorescence emission intensity at a reflection interface between higher and lower index materials. In these other labeled examples, the light need not be polarized.

SUMMARY

The present invention provides for total internal reflection ellipsometry without the use of prisms or gratings in a multiwell plate, thereby allowing for cost effective solutions for scaling the measurement in a way previously unimagined. If the dimensions of posts are chosen so that a beam of light can be introduced through the posts in a manner to achieve total internal reflection from the side walls of the posts, ligands immobilized on the exterior face of each post will be in an evanescent field which enables binding events between ligands and analytes in a biological sample in the well to be imaged simultaneously. In one application, the plurality of ligands form an array within each well where there are multiple posts per ligand spot. However, for larger configurations, it is possible to have arrays of ligands printed on the side walls of each post. The resulting image data is compared to a stored image of the polarization phase distributions in the beam obtained prior to the exposure of the ligand array to a sample in order to analyze the binding from the analytes in the samples.

The provision of solid transparent posts in the wells of a multiwell plate not only permits simultaneous imaging of binding events without the necessity of a tag (e.g., fluorescent, chemiluminescent, radioactive or otherwise) but also enables the placement of an array of separate ligands for each well of a plate. This configuration allows for simultaneous multiplexed assays for a number of patients for clinical diagnostics applications in one example. For rectangular posts with four walls, one embodiment includes the immobilization of a single ligand to each wall making four ligands per post. With, for example, 1000 posts in every well, for a ninety-six well plate, 384,000 individual ligand/analyte interactions can be measured in a single disposable. This represents a substantial increase in the number of possible multiplexed assays provided along with a significant reduction in the cost per assay. The formation of ligand arrays on upright walls of posts and the use of imaging ellipsometry to image binding events at the arrays thus represents a significant advance in the art.

The present invention also reduces a characteristic problem in evanescent field detection technologies, which is the problem of sediment from a sample falling down onto the detection area during measurement. Applications involving open well plates require that the plates be oriented with the open end upward. Having ligands at the bottom of open wells oriented in this manner exacerbates the sediment problem but this problem can be overcome with an array of ligands on the side wall as disclosed in the present invention.

In one embodiment, a transparent disposable multiwell plate has a pattern of wells, identical to the pattern commonly used in commercial multiwell plates. But in accordance with the present invention, each well includes a plurality of solid transparent posts each of a height equal to the height of the wells in one example. The wells and posts may be formed as a single part out of glass or plastic such that the height of the posts and the wells defines the thickness of the sample region which is enclosed after the bonding with a second plate. An array of ligand patterns is formed on the planar walls of the posts so that the reflected light from each post provides information regarding the interaction of analytes in solution to a plurality of different ligands.

Figure 1:
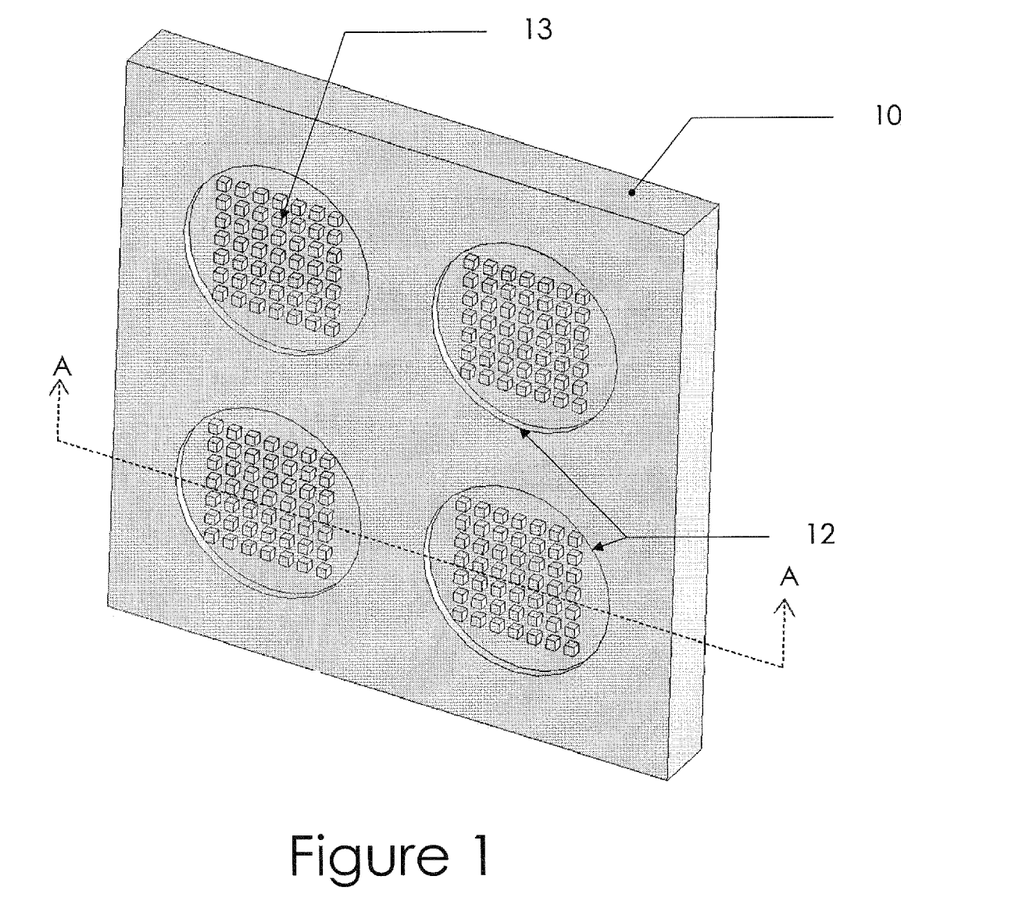
FIG. 1 is a perspective top view of a portion of a multiwell disposable.

In a second embodiment, microarrays are formed on the exterior surfaces of the posts, conveniently by printing, as shown in FIG. 1 where the half circles represent the ligand spots immediately after printing and before drying or washing. A second transparent plate is bonded to the first plate to seal the wells. In one example, the second plate has at least a pair of through holes aligned with each well in the first plate. The arrangement of holes allows for both the introduction of a sample into a well and the escape of excess sample material from the same well.

The lateral dimensions (x and y) and the height of each post herein are chosen to allow a beam of light to be directed to a post (e.g., into the bottom of each post) in a manner to achieve total internal reflection (TIR) from the (interior) face of at least one sidewall of a post and to produce an evanescent field in the plane of the immobilized ligands on the exterior face of that wall.

The microarrays conveniently comprise different ligands immobilized in rows and columns such that the individual ligands are associated with position information useful to identify the positions in the array at which binding events occur. The invention herein takes advantage of such arrays which can be printed within each well.

Ligands on a selected post may be accessed by a collimated, polarized beam individually, or all the like-facing arrays on all posts in, for example, rows of wells may be accessed simultaneously. Also, ligands on posts may be accessed sequentially by reorienting the disposable with respect to the light source and imaging system (or vice versa) or by scanning individual spots using a laser.

Also, in one embodiment, the posts are coated with a metallic film and the angle of the light source is varied to produce surface plasmon resonance at the SPR angle.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides an advantageous apparatus and method for performing ligand binding assays using microarrays in a multiwell plate format. Prior to describing embodiments of the present invention in detail, the following definitions are provided for use throughout the present document.

DEFINITIONS

Microwell Plate: A flat plate with multiple "wells" used as small test tubes. The microplate has become a standard tool in analytical research and clinical diagnostic testing laboratories with 6, 24, 96, 384 or even 1536 sample wells arranged in a 2:3 rectangular matrix in one example.

Ligand: Any molecule that binds to another, in normal usage a soluble molecule such as a hormone or biological molecule that binds to a binding partner or capture molecule. The decision as to which is the ligand and which is the capture molecule is often arbitrary. In the sense of this invention, the ligand refers to that binding element attached to a planar surface and which binds to an analyte molecule in a biological sample.

Total Internal Reflection (TIR): An optical phenomenon that occurs when light strikes a medium boundary at a steep angle. If the refractive index is lower on the other side of the boundary (i.e., the side that doesn't directly receive the light) no light can pass through and effectively all of the light is reflected. The critical angle is the angle of incidence where total internal reflection begins and continues up to angles of incidence of 90 degrees.

Ellipsometry: A very sensitive optical measurement technique providing unequalled capabilities for thin film analysis utilizing the change of polarization of light which is reflected off a sample or transmitted through a sample.

Surface Plasmon Resonance (SPR): The excitation of surface plasmons by light is denoted as a surface plasmon resonance for planar surfaces. Plasmons are collective oscillations of large numbers of electrons in matter, mostly in metals.

Arrays: Ligands affixed to a surface at separate localized regions called spots in an ordered manner thus forming a microscopic pattern where ligand identity is determined by the location (or "address") of that particular spot.

Binding Protein (Ligand) Assay: A test that uses the binding of proteins (e.g., antibodies) to other ligands (e.g., antigens) to identify and measure the concentration of certain biological substances in blood, urine or other body components. Ligand assays may be used to diagnose disease, drug or vitamin levels, response to therapy or other information of biological relevance. Also, test results can provide information about a disease that may help in planning treatment (for example, when estrogen receptors are measured in breast cancer).

Figure 2:
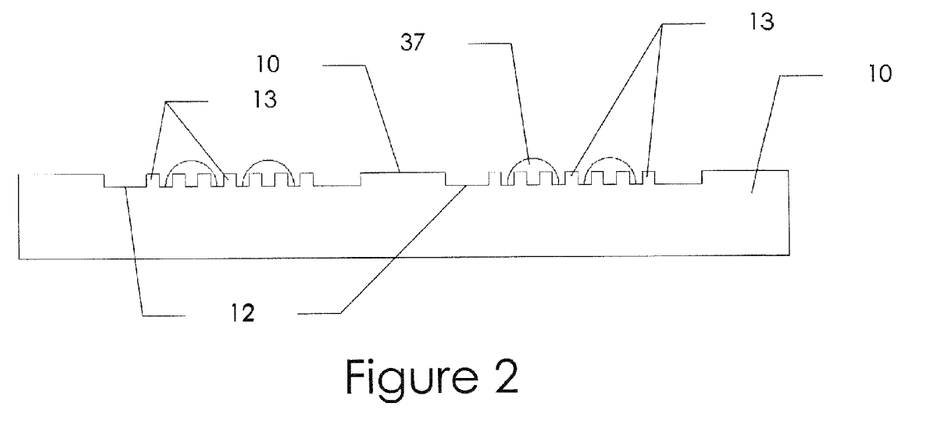
FIG. 2 is a sectional view of a portion of the multiwell disposable illustrated in FIG. 1 in accordance with the principles of this invention.

FIG. 1 is a perspective top view of a transparent plate 10 that is a portion of a multiwell disposable, and FIG. 2 is a sectional view of plate 10 along line A-A illustrated in FIG. 1 in accordance with the principles of this invention. Plate 10 has an array of wells 12 formed therein and each well includes a plurality of solid posts 13. In one example, there may be 49 posts in each well. In one embodiment, plate 10 will have 96 or 384 wells and have the overall dimensions of 12.8 cm by 8.6 cm with a plate thickness of roughly 1 mm so that the lateral dimensions are in conformance with dimensions of available multiwell disposables.

For a 96-well plate as an example, a well has dimensions of 7 mm by 7 mm for square wells or a diameter between 6 and 7 mm for circular wells, and each post is solid and has a height between about 25 µm and about 100 µm to be substantially equal to the depth of the shallow wells. The four well section of plate 10 which is shown in FIG. 1 illustratively has dimensions of 9 mm by 9 mm in the 384-well example and 18 mm by 18 mm in the 96-well example.

Figure 3:
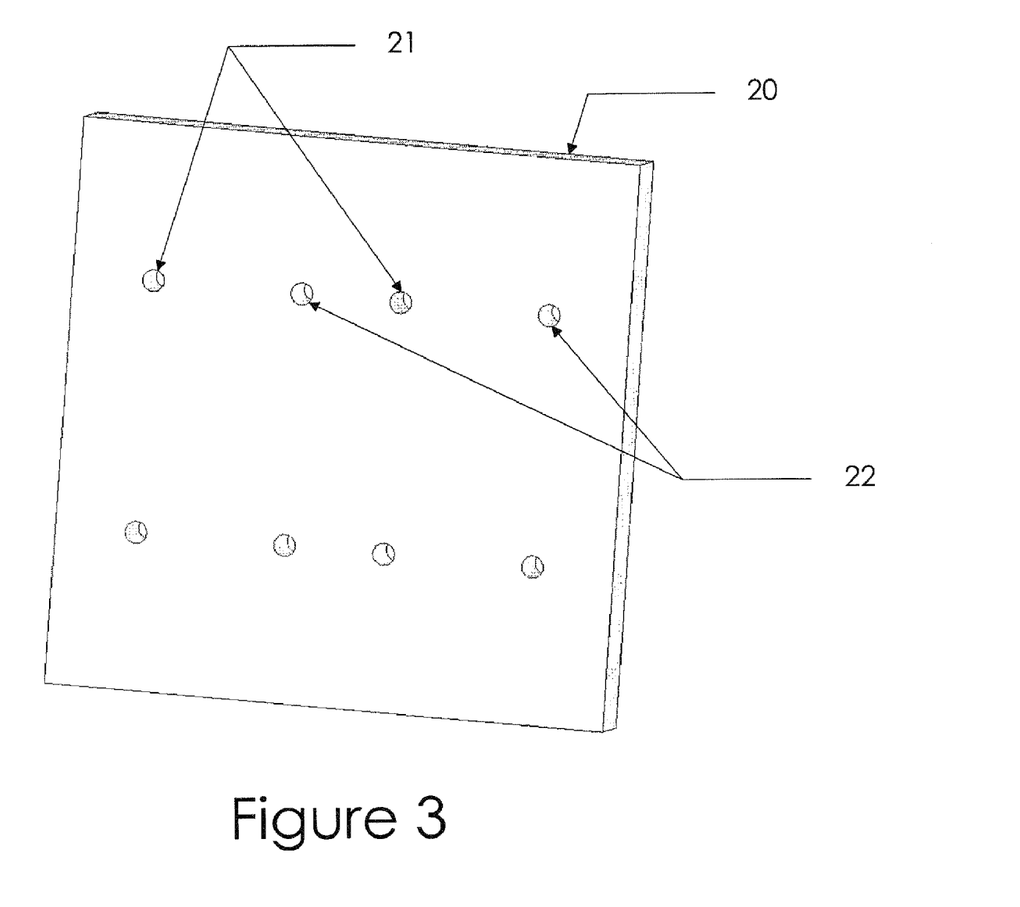
FIG. 3 is a perspective view of a cover plate to be juxtaposed with the portion of FIG. 1 to form a sealed disposable.

FIG. 3 shows a plate 20 which has dimensions equal to those of plate 10. Plate 20 is juxtaposed with and bonded to plate 10 in a manner to substantially cover or seal wells 12 (see, e.g., FIG. 4). The two plates 10 and 20 have the same index of refraction and are bonded together with known techniques to avoid optical reflection at the interface. In this particular design, plate 20 includes a pair of through holes 21 and 22, with each pair in registry with a well. Illustrative pairs of holes are shown in FIG. 3 and correspond to each of the four wells of FIG. 1. The through holes provide access for the introduction of a sample into a well and for excess sample material to escape the well. Various designs may be used for plate 20 to allow a continuous flow of liquid or gas into one hole while the gas or liquid inside may be exchanged.

Figure 4:
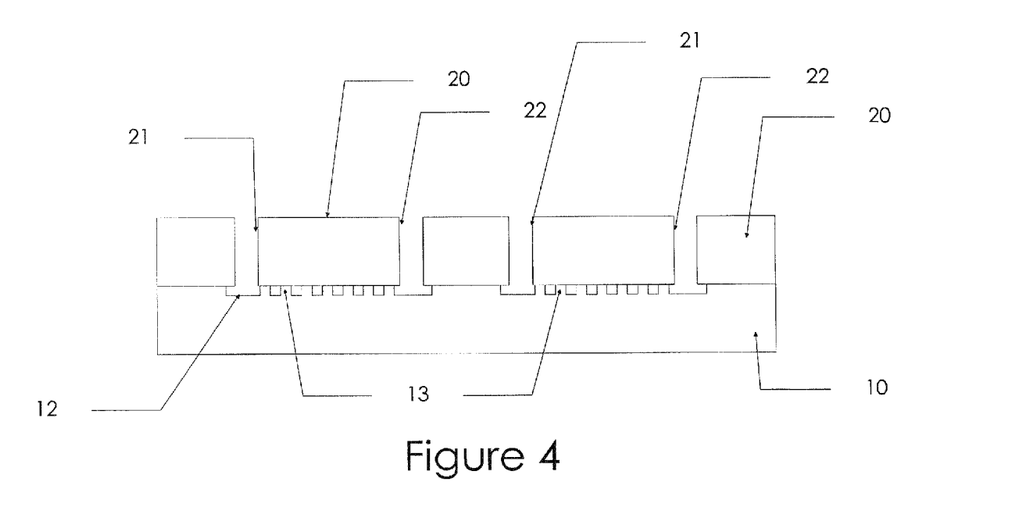
FIG. 4 is a schematic side view of two wells of a sealed disposable with the portions of FIG. 1 and FIG. 3 in mated positions.

FIG. 4 shows a schematic side view of two wells 12 with plates 10 and 20 joined together. It should be understood that the wells and the posts are of like height and so are optically continuous with plate 20 in one embodiment. The purpose of this is to allow any light which reflects from a post side wall to be transmitted through plate 20 and out of the plate for detection.

Figure 5:
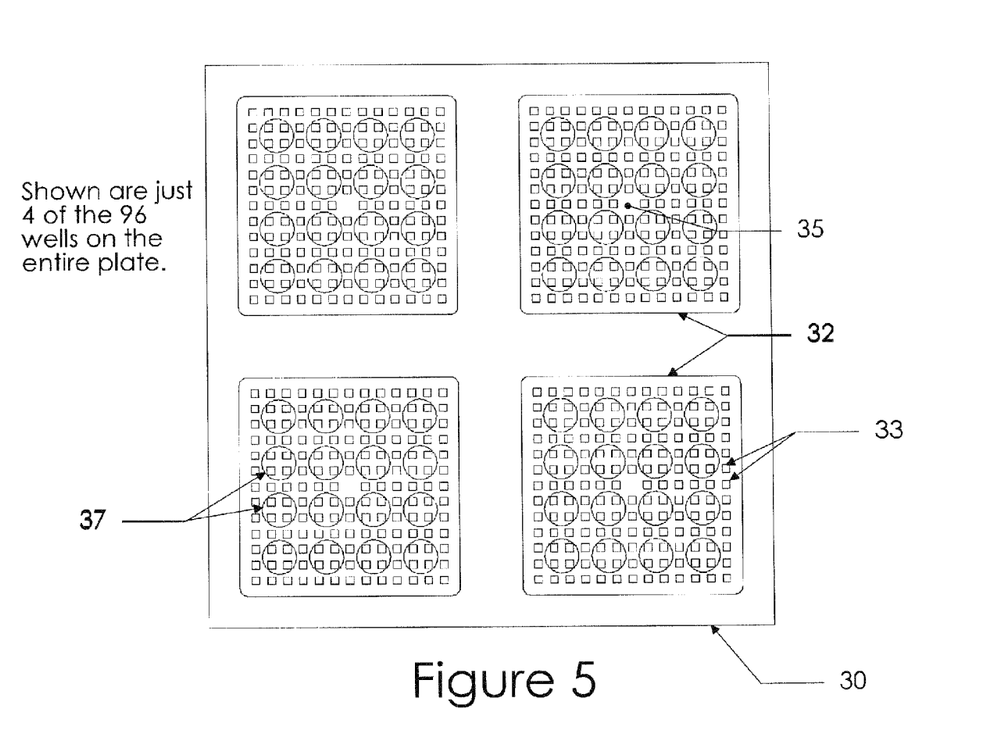
FIG. 5 is a top view of a portion of a multiwell disposable in accordance with another embodiment of the present invention.
Figure 6:
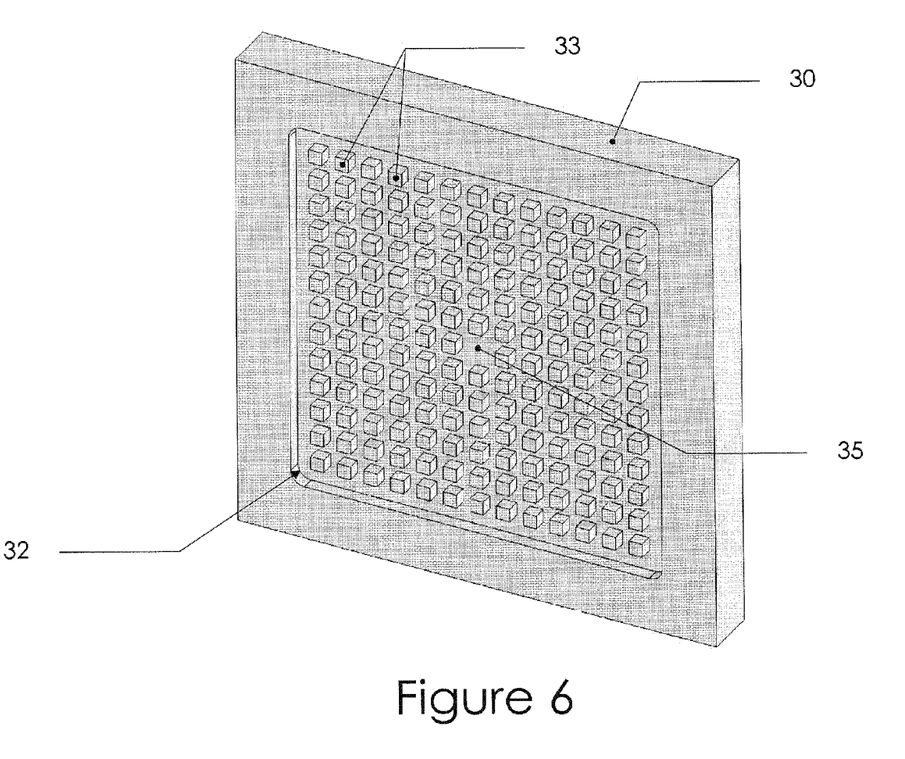
FIG. 6 is a perspective view of a single well of the multiwell disposable portion of FIG. 5 including a plurality of posts in accordance with this invention.

FIG. 5 is a top view of a transparent plate 30 that is a portion of a multiwell disposable in accordance with another embodiment of the present invention, and FIG. 6 is a perspective view of a single well 32 of the multiwell disposable portion of FIG. 5. As shown in FIGS. 5 and 6, wells 32 have a square well design in accordance with this embodiment. Wells 32 are formed in plate 30 and can be seen to include a plurality of posts 33 shown, illustratively, in an array pattern. In one example, each well includes a 13×13 array of posts 33 and has dimensions of 7 mm×7 mm in this particular design with each post having dimensions to permit TIR as described hereinbefore. A space 35 is provided, conveniently, in the center of the array to align with the hole of a cover plate (see, e.g., FIG. 7) which will act as the guide for sample entry.

The embodiment as shown in FIGS. 5 and 6 can be adapted to a multiwell plate in which each well has a relatively large number of posts. It is possible in one embodiment for the ligand spots to be smaller than the dimensions of the posts. In this embodiment, one may print ligand arrays on the side walls of the posts. Since typical ligand spots are on the order of 100 microns, this would be more practical with posts having at least one dimension greater than three times the diameter of a spot or greater than 300 microns in this case. For example, for 2D arrays on sidewalls, posts could be 1 cubic millimeter with each side wall containing 25 ligand spots. For 1D arrays, the posts can be made 100 microns high, 100 microns thick, and 1 mm wide to accommodate five spots on the longer side wall. Minimizing the height of the posts is advantageous for allowing one to use very small sample volumes.

In another embodiment of the type shown in FIGS. 5 and 6, the post dimensions are smaller than the dimensions of microarray spots. Ligand spots may be introduced to subsets of the posts in a well where they completely cover multiple posts (e.g., see spots 37 in FIGS. 2 and 5). The surface of plate 30 is treated with a surface chemistry which binds target ligands. The ligand spots dry on the posts leaving the post top and sidewalls coated with a single ligand. There are still multiple ligand arrays per well since each spot 37 may be a different ligand but not per post as in the first embodied description. Accordingly, each spot 37 occupies a known position. In this illustration, sixteen ligand spots are shown for each well and, thus, up to sixteen individual tests can be carried out for each sample introduced into a well in this particular design. Any binding which occurs between an analyte in the sample and the ligands of a spot will occur at a known (spot) position.

Figure 7:
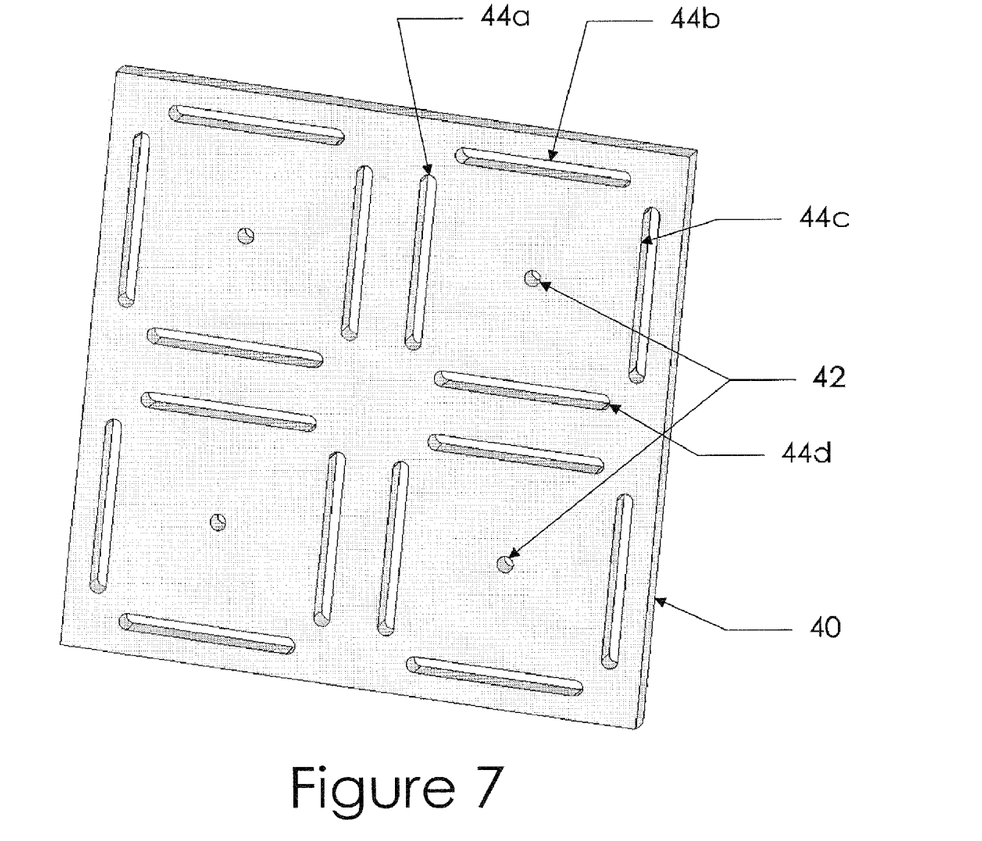
FIG. 7 is a perspective view of a cover plate for the embodiment illustrated in FIGS. 5 and 6.

After the ligand spots dry, plate 30 is rinsed thoroughly to remove excess material and a cover plate 40 of FIG. 7 is bonded to plate 30 to seal the wells. In this particular design, plate 40 includes a center hole 42 in registry with each square well and four exit slits 44a, 44b, 44c, and 44d per well to allow uniform flow of fluid radially from the square well centers. Through holes 42 are aligned with space 35 (FIGS. 5 and 6) for the introduction of a sample to the well. Plate 40 would have dimensions equal to plate 30 (FIG. 5) for this design and be bonded in a manner substantially similar to what was described previously. The inside border of the four slits 44a-44d is interior to the outer border of each well 32 in FIG. 5 so that air and fluid are allowed to escape during filling. Advantageously, FIG. 7 illustrates a cover plate 40 with a practical arrangement for fluid entry and exit apertures for a four well embodiment.

It is to be understood that the use of posts in a well, in accordance with the principles of this invention is practical whether a plurality of like ligands or an array of ligand patterns are immobilized on post sidewalls (and tops) or whether the posts are smaller or larger than the dimensions of the ligand spots.

Figure 8:
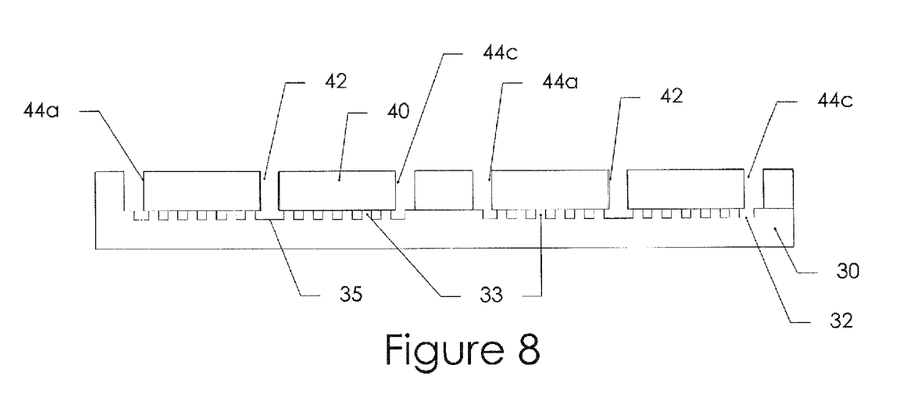
FIG. 8 is a schematic side view of two wells of a sealed disposable with the portions of FIG. 5 and FIG. 7 in mated positions.

FIG. 8 shows a schematic side view of two wells 32 with plates 30 and 40 joined together and hole 42 aligned with space 35 and slits 44a and 44c properly aligned.

Figure 9:
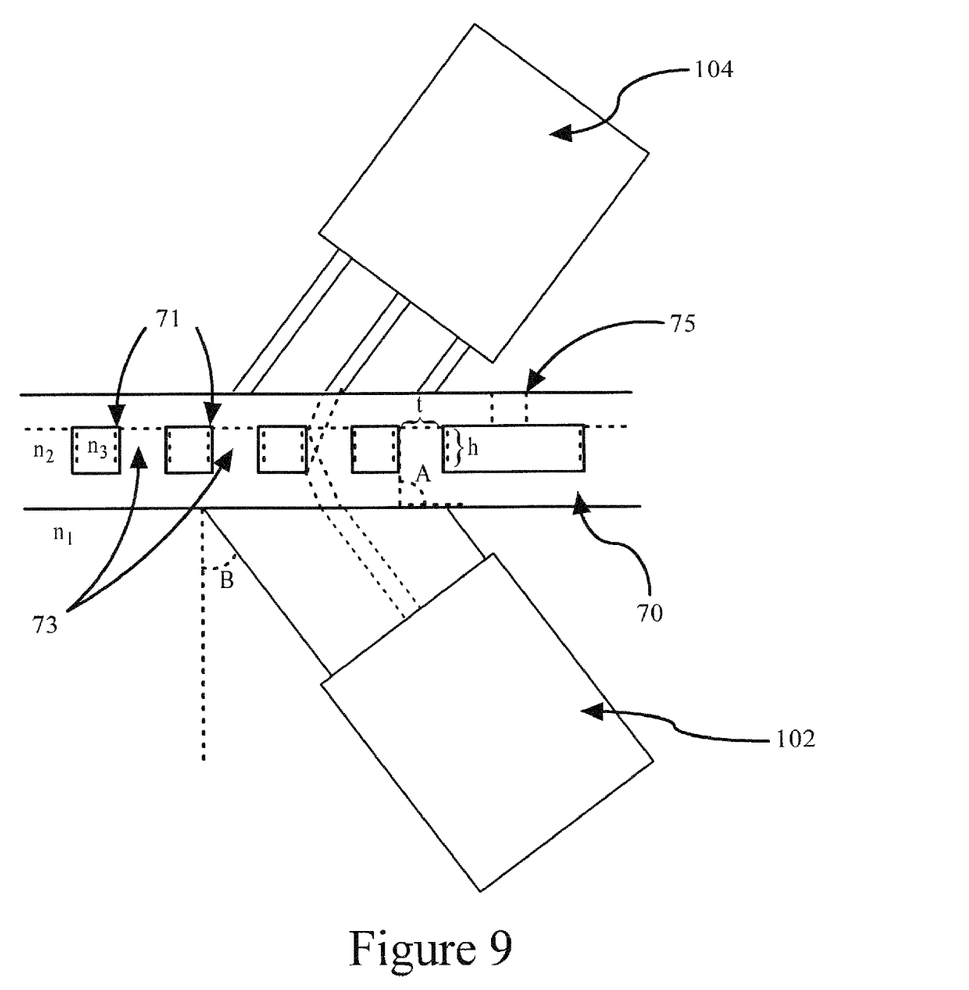
FIG. 9 is a schematic representation of the interrogation and imaging system for sensing binding events with the disposable of FIGS. 1, 2, 3 and 4 or of FIGS. 5, 6, 7 and 8.

FIG. 9 shows illustrative posts 73 with arrays 71 of ligands immobilized on the exterior of two walls of each post. It should be understood that other walls may also be utilized. It is also to be understood that the patterns of ligands are immobilized in an array in which the position of a ligand(s) in the array is significant. The reason for this is that a binding event between a ligand and an analyte in a sample in a well causes a change in the relative phase between s- and p-polarized reflected light at that position. In accordance with this invention an image of all those phase changes is compared with a stored initialized image to determine which analytes are present in a sample.

FIG. 9 shows a light source 102 and an imaging system 104 operative to direct a beam of polarized light at a wall of a post 73 in a manner to generate an evanescent field in the plane of the ligands. Analytes in a sample introduced into a well through, for example, an aperture 75 will bind with different patterns of ligands in the array providing for localized intensity changes in the reflected light at the positions of the ligands effected. Examples of applicable light sources and imaging systems are disclosed in the above-noted U.S. Pat. No. 6,594,011, which has been previously incorporated by reference herein.

In one example, in order to image binding events, the ligand array is accessed by collimated, polarized light directed from below plate 70 at a post wall in a manner to obtain TIR at the wall. This is to be contrasted with previous arrangements typical in the art operative to achieve TIR at the horizontal bottom surface of the plane on which ligand arrays are immobilized.

In order to achieve total internal reflection (TIR) for imaging the pattern of binding events on a wall of a post in the array of wells of FIG. 9, the indices of refraction of the materials as well as the angle between the transmission surface and the TIR surface is important because TIR cannot occur unless the following equation is satisfied:

$$\sin(A) * \sqrt{n_2^2 - n_1^2 \sin^2(B)} - \cos(A) * n_1 \sin(B) \geq n_3$$

where A is the angle between the transmission surface contacting air and the TIR surface contacting the sample, B is the incidence angle of the light in air, $n_1$ is the index of refraction of air, $n_2$ is the index of refraction of the transparent material of the plate and $n_3$ is the index of refraction of the sample (water, blood, urine, etc.). This formula simplifies dramatically if the wall of the well is normal to the bottom of the plate since then A=90° and the second term in the above equation vanishes. The resulting equation becomes:

$$\sin(B) \leq \frac{1}{n_1} \times \sqrt{n_2^2 - n_3^2}$$

In one embodiment compatible with current multiwell plate technology, individual wells of the plate are spaced according to Ansi/SBS standards (e.g., 4.5 mm center to center for 384 well plates and 9 mm center to center for 96 well plates). The spacing of the wells is true to standard. But, in accordance with the principles of this invention, the addition of posts to a well and the dimensions of individual posts are important. In fact, there is a minimum post thickness in at least one dimension to allow total internal reflection to occur at precisely the critical angle from the side wall in such a way that the entire surface may be illuminated. This minimum post thickness depends on the index of refraction of the plate, the index of refraction of the material inside the wells during a measurement, and the height of the posts. The formula for post thickness in the direction of light propagation is the following:

$$t \geq \frac{h\sqrt{n_2^2 - n_3^2}}{n_3}$$

where t is the post thickness, h is the post height, $n_2$ is the index of refraction of the plate and $n_3$ is the index of refraction of the (sample) material inside the well during measurement. All variables in the equation are labeled in FIG. 9. For example, for plastic plates having a refractive index of 1.49, a post height of 75 microns, and a liquid sample of index 1.34, the minimum thickness is 36.5 microns. For refractive indices of acrylic plates and typical biological fluid samples, the height of the posts cannot be much more than double the post thickness. For simplicity, all of the Figures including posts within sample wells are drawn with t=h since this is a convenient geometry for purposes of illustrating certain embodiments. Additionally, TIR would work for any index below 1.34 for the sample material since the same angle would be in the TIR region. For polycarbonate plates of index 1.59 and the same liquid sample, the minimum thickness of a 75 micron high post would be 47.9 microns if imaging is needed all the way to the TIR angle in such a way that the entire side wall is illuminated.

The manner in which the arrays are printed is well understood and described in the literature on topics dealing with technological aspects of DNA and protein microarrays. Contact and non-contact printing techniques for ligands are applicable. Ligands may be immobilized on all the (exterior) walls of a post or several posts with a small drop of solution larger than the dimensions of the individual posts. However, when plates 10 and 30 are joined, the array on the top of a post becomes inaccessible and does not affect signals generated in the light reflected from a side wall since the refractive index of the protein is close to the curing adhesive which binds the two parts together. Furthermore, optical thin films may be provided on the sidewalls to amplify signals within the evanescent field region on those surfaces.

The interrogating beam from source 102 may be directed at the (ligand) wall of a single post or simultaneously at the (ligand) walls of a plurality of posts which are in the cross section of the collimated beam. Moreover, the beam may be redirected by conventional implementations (i.e., small scanning mirrors) to access all the wells of each of a sequence of rows and columns of FIG. 1 or 6.

In accordance with another embodiment of the present invention, the apparatus of FIGS. 1-9 can be used also in conjunction with an optical system employing surface plasmon resonance (SPR) to sense the binding events between analytes in a sample and the ligands of an array. In this embodiment, a metallic film (not shown) of gold, silver, or copper, typically ~50 nm thick in the case of gold, is formed on the sidewall faces of posts and ligand arrays are immobilized afterward within each well. The interrogating light beam is directed at a post wall at an angle within the TIR regime in a manner to produce surface plasmons within the metal film with a characteristic evanescent field which interacts with the plane of the array. In this embodiment, the beam angle is no longer the critical angle but the SPR angle within the TIR regime as is well understood in the field.

The disposable multiwell plate in accordance with the present invention has a number of differences and benefits over prior uses of imaging ellipsometry.

1. It is clear that the apparatus and method herein disclosed comprises a disposable multiwell plate which has dimensions compatible with robotic instrumentation currently in use with multiwell plates.
2. The disposable multiwell plate is employed similar to commercially available multiwell plates in terms of manual or automatic fluid dispensing.
3. No prism or index matching oils are necessary for the user to achieve total internal reflection.
4. Signal is far less sensitive to false readings by sediment falling out of solution.
5. Completely separate assays can be achieved within the same plate simply by rotating a multiple of 90 degrees or reading the plate from different side walls of the posts.
6. Significantly more imaging or scanning area is now achievable without the expense of the large optics (e.g., 8") otherwise required or an array of small prisms accurately aligned underneath each well or row of wells.

7. Because the ligands are sealed inside a microfluidic multiwell plate, the disposable does not need to be stored in a clean air environment as is the case with open multiwell plates with ligands on the bottom of wells which could collect dust. For ellipsometry, surfaces need to be kept very clean and this is one of the reasons why ellipsometry has not been used in conventional diagnostics in the past.

8. For the microfluidic embodiment in particular, fluid volumes are only 2.5 µl per well for 96-well plates and 450-600 nl per well for 384-well plates. Typical volumes are around 100 µl per sample and it is advantageous to use the least amount of sample as possible for expensive samples.

9. The thin, planar design (~2-3 mm thick) of the microfluidic embodiment allows numerous plates to be stacked for high throughput applications. For example, 100 stacked plates is only about 1 foot high and could include tests for 38,400 patients.

In the case of the imaging system 104, the camera itself need not be a sophisticated, high resolution CCD camera if, indeed, relatively few ligands are immobilized on each ligand wall as would be the case for most current diagnostic use. In such cases on the order of a few to tens of ligands need be immobilized for diagnostic purposes. This lower demand for content translates to less expensive cameras and more cost-effective systems configured for doctor offices and clinical laboratories performing diagnostic testing. For other purposes such as biological research in metabolic or cancer pathways, drug target interactions in drug discovery, and biomarker profiling during clinical development of new therapeutics, higher content of ligands in arrays (100's to 1000's) may be required.

In one embodiment, the invention has been described in terms of total internal reflection ellipsometry employing polarized light and sensing localized changes in the phase of s- and p-polarized light. In another embodiment, SPR has been utilized. In yet another embodiment, the entire system may be used for sensing labeled targets as well by placing a filter in front of the detector to block the reflected light and transmitting only the light emitted from the fluorophore as is done with commercial microarray scanning systems. It is intended that the invention herein applies to labeled as well as unlabeled systems. It will be further apparent that various existing analytical techniques and future analytical techniques in conjunction with the side wall concept are within the scope of the present invention.

What has been described is considered merely illustrative of the invention herein and it is apparent that various modifications thereof may be devised by those skilled in the art still without departing from the spirit and scope of the invention as encompassed by the following claims. For example, a post need not be rectangular in shape. It need only have at least one planar wall on which ligands are immobilized. If more than one wall of a post is planar, ligands can be immobilized on each planar wall and the plate can be reoriented with respect to the light source and imaging system (or vice versa in which the light source and imaging system can be reoriented with respect to the plate) to produce the requisite TIR operation. Also, although simultaneous access of multiple ligand arrays as well as scanning from one ligand array to another have been described herein, it is contemplated that the individual spots of an array can be scanned in the manner described herein, for example, by a laser. Consistent with conventional multiwell plate usage, the wells may be left open or the well array may be sealed as described herein.

What is claimed is:

1. An apparatus, comprising:
a first transparent planar plate having at least one well therein, the well including a plurality of transparent upstanding posts therein,
wherein each of the plurality of posts has a planar sidewall and is of a material and has cross-sectional dimensions and a height to permit a beam of light directed into the post to produce total internal reflection in a manner to produce an evanescent field at the sidewall.

2. The apparatus as in claim 1, wherein the posts are coated with a ligand.

3. The apparatus as in claim 1, wherein the plurality of posts is organized in a set of arrays, each array of a set being coated with a different ligand.

4. The apparatus as in claim 1, wherein the plurality of posts is organized in subsets and each of the subsets is coated with a different ligand.

5. The apparatus as in claim 1, wherein each of the posts has a rectangular cross section with four planar walls.

6. An apparatus, comprising:
a first transparent planar plate having at least one well therein, the well including a plurality of transparent upstanding posts therein, wherein the posts are coated with a ligand; and
a second transparent plate juxtaposed with the first plate in a manner to seal the well wherein the second plate includes a hole aligned with the well.

7. The apparatus as in claim 1, further comprising a plurality of wells, each of the wells comprising a plurality of solid transparent upstanding posts organized in a plurality of arrays wherein the posts of each array is coated with a different ligand.

8. The apparatus as in claim 6, further comprising a source of a beam of light and means for directing the beam into a post of the plurality of posts in a manner to generate an evanescent field at a sidewall of the post.

9. The apparatus as in claim 8, further comprising means for capturing the image of light reflected from the sidewall.

10. An apparatus, comprising:
a first transparent planar plate having a plurality of wells, each of the wells comprising a plurality of transparent upstanding posts organized in a plurality of arrays wherein the posts of each array is coated with a different ligand,
wherein each of the posts in each of the wells has a planar sidewall and is of a material and has cross sectional dimensions and a height to permit a beam of light directed into a post to produce total internal reflection in a manner to produce an evanescent field at the sidewall of the post.

11. The apparatus as in claim 10, further comprising a second transparent plate juxtaposed with the first plate in a manner to seal the wells wherein the second plate includes a plurality of through holes, each hole being aligned with one of the wells to permit the introduction of a sample into a well.

12. An apparatus, comprising:
a first transparent plate having at least one well therein, the well including at least one upstanding post, wherein the at least one upstanding post is coated with a ligand; and
a second plate juxtaposed with the first plate in a manner to seal the well, wherein the second plate includes a through hole for introducing a sample into the well.

13. The apparatus as in claim 12, wherein the post has at least one planar sidewall and is of a material and geometry to permit a beam of light to be diverted into the post in a manner to generate an evanescent field at the planar sidewall.

* * * * *